United States Patent [19]

Welker

[11] Patent Number: 4,628,750
[45] Date of Patent: Dec. 16, 1986

[54] INTEGRATED PUMP AND SAMPLE VESSEL

[75] Inventor: Brian H. Welker, Houston, Tex.

[73] Assignee: Welker Engineering Company, Sugar Land, Tex.

[21] Appl. No.: 654,937

[22] Filed: Sep. 27, 1984

[51] Int. Cl.$^4$ .............................................. G01N 1/14
[52] U.S. Cl. .............................. 73/864.63; 73/863.71; 73/864.34; 73/864.62
[58] Field of Search ........... 73/864.35, 864.34, 863.83, 73/863.84, 863.71, 863.72, 863.73, 864.63, 864.62

[56] References Cited

U.S. PATENT DOCUMENTS

| | | | |
|---|---|---|---|
| 2,637,211 | 5/1953 | Norman, Jr. ...................... | 73/864.34 |
| 2,925,735 | 2/1960 | Topp et al. .................. | 73/863.84 X |
| 3,390,580 | 7/1968 | Taylor .............................. | 73/864.34 |
| 3,782,198 | 1/1974 | Wächter et al. ................. | 73/864.34 |
| 3,789,670 | 2/1974 | Rosenwald ...................... | 73/864.62 |
| 3,819,330 | 6/1974 | Creighton ..................... | 73/863.83 X |
| 3,850,036 | 11/1974 | Sanctuary et al. ........... | 73/864.34 X |
| 3,862,575 | 1/1975 | Thompson et al. .............. | 73/864.35 |
| 3,945,770 | 3/1976 | Welker ................................. | 417/401 |
| 4,172,670 | 10/1979 | Welker ........................... | 73/864.62 X |
| 4,283,949 | 8/1981 | Hulme ............................... | 73/864.34 |
| 4,403,518 | 9/1983 | Welker ............................. | 73/864.34 |
| 4,440,032 | 4/1984 | Welker ......................... | 73/864.34 X |
| 4,470,773 | 9/1984 | Welker ......................... | 73/864.62 X |

FOREIGN PATENT DOCUMENTS

| | | | |
|---|---|---|---|
| 1498969 | 11/1968 | Fed. Rep. of Germany ... | 73/864.34 |
| 2070769 | 9/1981 | United Kingdom ............. | 73/864.34 |

OTHER PUBLICATIONS

Welker Engineering Company Publication; By Jun. 1979.
"Proper Sampling Key to Measuring Mixes of Light Hydrocarbons"; The Oil and Gas Journal, pp. 204, 207, and 209; Sep. 19, 1977; N. Broussard.
"Techniques of Gas Sampling" pp. 48-68; article by Charles F. Drake of Natural Gas Pipeline Company of America et al.; published between Mar. 1979 and May 1986.

Primary Examiner—Stewart J. Levy
Assistant Examiner—Tom Noland
Attorney, Agent, or Firm—Gunn, Lee & Jackson

[57] ABSTRACT

An integrated pump and sample vessel which eliminates dead volume between the point of collection of the sample and the sample vessel. The pump has a body with a longitudinal bore therethrough, a fluid flow passage in the body which allows fluid to enter and exit the pump, a resilient member located in the bore which has a face with a cavity therein exposed to the fluid flow passage and a sleeve which confines the resilient member. A sample vessel is adapted to be detachably mounted to the pump body with a face exposed to the fluid flow passage. A check valve is located in the sample vessel to selectively enable the entry of fluid from the flow passage of the pump. In the preferred embodiment, the check valve is located in an easily removable pod to facilitate service or adjustment. A diaphragm motor or other moving apparatus drives the face of the resilient member into contact with the face of an adapter or the face of the sample vessel which traps a sample of fluid in the cavity. The moving apparatus applies greater pressure and resiliently collapses the cavity which pumps sample past the check valve into the sample vessel.

19 Claims, 6 Drawing Figures

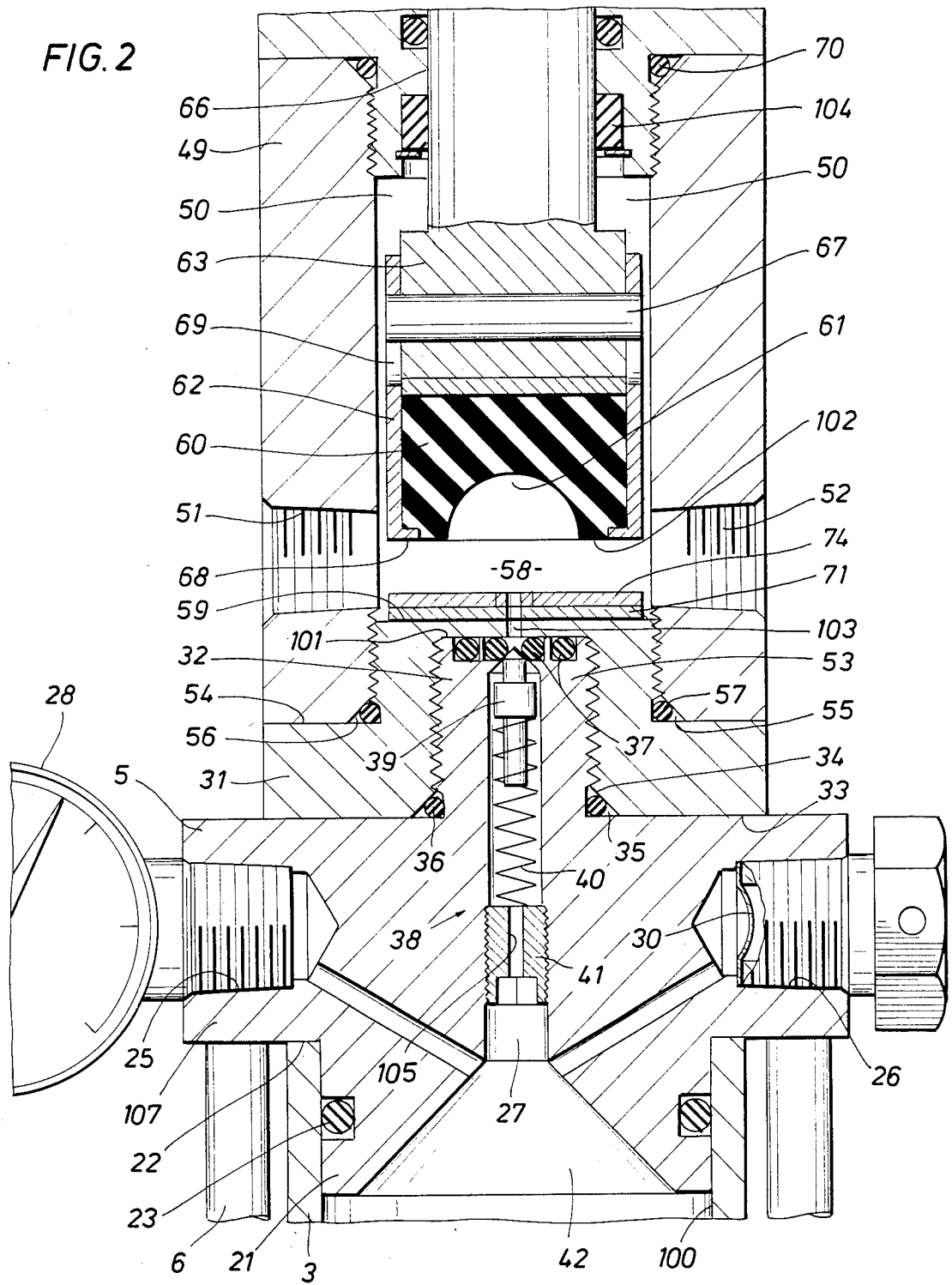

INTEGRATED PUMP AND SAMPLE VESSEL

BACKGROUND OF THE DISCLOSURE

1. Field of Invention

The integrated pump and sample vessel disclosed in this invention are typically used to take aliquot samples from hydrocarbon pipelines at any point from the producing well to the location of the end user.

2. Description of the Prior Art

High pressure pumps have been disclosed in U.S. Pat. No. 3,945,770 by Robert H. Welker. Improvements in this apparatus are further disclosed in U.S. Pat. No. 4,403,518 and pending applications Ser. No. 456,328, now U.S. Pat. No. 4,557,151 and Ser. No. 222,362, now U.S. Pat. No. 4,525,127 also by R. H. Welker. These pumps have been used to place odorants and hydrate inhibitors in natural gas pipelines; they have also been used in cryogenic service to pump liquid carbon dioxide. They have been used in other applications to pump various fluids, i.e., water.

Pumps of this type are widely used to take samples of natural gas for laboratory analysis of the BTU content of the natural gas. For many years, natural gas was sold merely by volume without regard to the BTU content. Today, almost every new contract involving the purchase or sale of natural gas will calculate the price based on both the volume and the BTU content. The volume of the gas is calculated by meter tubes, orifice plates and other means well known in the art. The BTU content of the gas is typically analyzed in a laboratory which is typically some distance from the well head, pipeline, or meter station. Samples are therefore taken and transported to the laboratory for analysis by calorimeter, gas chromatograph and other means well known in the art. It has therefore become extremely critical for the samples to be substantially representative of the product that is being bought or sold. A slight difference in BTU content can make an enormous difference in price.

The high pressure pumps of the prior art generally have a dead volume in the body of the pump between the point of sample collection and the outlet located on the valve body. This dead volume is typically increased because of the piping necessary to connect the sample vessel to the outlet on the pump. One object of the present invention is to eliminate any dead volume in the pump between the point of collection and the sample vessel.

When the high pressure pump as disclosed in the Welker '770 Patent was used to sample crude oil, there was no effective way to purge the dead volume in the valve body between samples. As a result, U.S. Pat. No. 4,440,032 was issued to Robert H. Welker for a sampler incorporating a purge system. Another object of the present invention is to eliminate the need for a purge system to flush the dead volume in the pump or the piping between the pump and the sample vessel.

Cylindrical sample collection vessels containing an internal piston which divides the vessel into two chambers have been used in the past in conjunction with pumps such as those disclosed in the aforementioned Welker Patents. Sample vessels similar to that shown in the present invention are disclosed in U.S. Pat. No. 4,459,865 by R. H. Welker. The subject of the present invention improves the design in the pump body and the sample vessel by integrating them into a single unit which eliminates dead volume between the point of collection of the sample and the sample container.

High pressure pumps of the type disclosed can create vacuums between various internal parts which may reduce the operational life of such internal parts. A vacuum breaker apparatus is disclosed in U.S. Pat. No. 4,470,773 which could be adapted for use in the present invention.

BRIEF SUMMARY OF THE DISCLOSURE

The present invention is summarized as an integrated pump and sample vessel which eliminates dead volume. A fluid to be sampled enters the pump through an inlet port and moves through a passage in the body of the pump and exits through the outlet port. The sample vessel is adapted to be removably mounted on the pump. The sample vessel threadably engages an adapter which threadably engages the body of the pump, exposing the face of the adapter to the passage. In the alternative, the sample vessel threadably engages the body of the pump, exposing the face of the sample vessel to the passage. A resilient member is located in the bore of the pump having a face with a cavity therein exposed to the passage. A pair of thin vacuum breaker plates extend across the face of the adapter or the face of the sample vessel. There is a tiny hole in the center of each plate which allows passage of fluid therethrough. The resilient member is confined by a hollow sleeve which prevents extrusion when the resilient member is compressed. The resilient member and hollow sleeve are attached to a shaft by a holding pin. A conventional moving means is used to actuate the shaft such as a diaphragm motor, solenoid, or electric motor. The moving means causes the shaft to advance the resilient member and hollow sleeve into direct contact with one of the vacuum breaker plates resting on the face of the adapter or the sample vessel. As greater force is applied through the shaft, the cavity in the face of the resilient member is collapsed forcing an aliquot sample through the holes in the vacuum breaker plates, past a check valve means into the sample vessel. After the sample passes by the check valve means, a temporary vacuum is formed between the face of the resilient member, the vacuum breaker plates and the face of the adapter or sample vessel. This temporary vacuum is caused in part because the resilient member has a memory and seeks to return to its uncompressed shape, and in part because the face of the resilient member is being moved away from the face of the adapter or sample vessel. As the shaft is retracted, the vacuum breaker plates rise ever so slightly with the resilient member and allow fluid to pass through the holes therein into the cavity on the face of the resilient member. The vacuum breaker plates pop off of the face of the resilient member and return to their normal resting location on the face of the adapter or sample vessel. In the preferred embodiment, the check valve means is located in an easily removable pod to facilitate service or adjustment.

BRIEF DESCRIPTION OF THE DRAWINGS

FIG. 2 is an enlarged view of the integrated pump and sample vessel from FIG. 1.

FIG. 3 is a top view of a vacuum breaker plate;

FIG. 4 is a top view of a second vacuum breaker plate;

DETAILED DESCRIPTION OF THE PREFERRED EMBODIMENT

Figure 1:
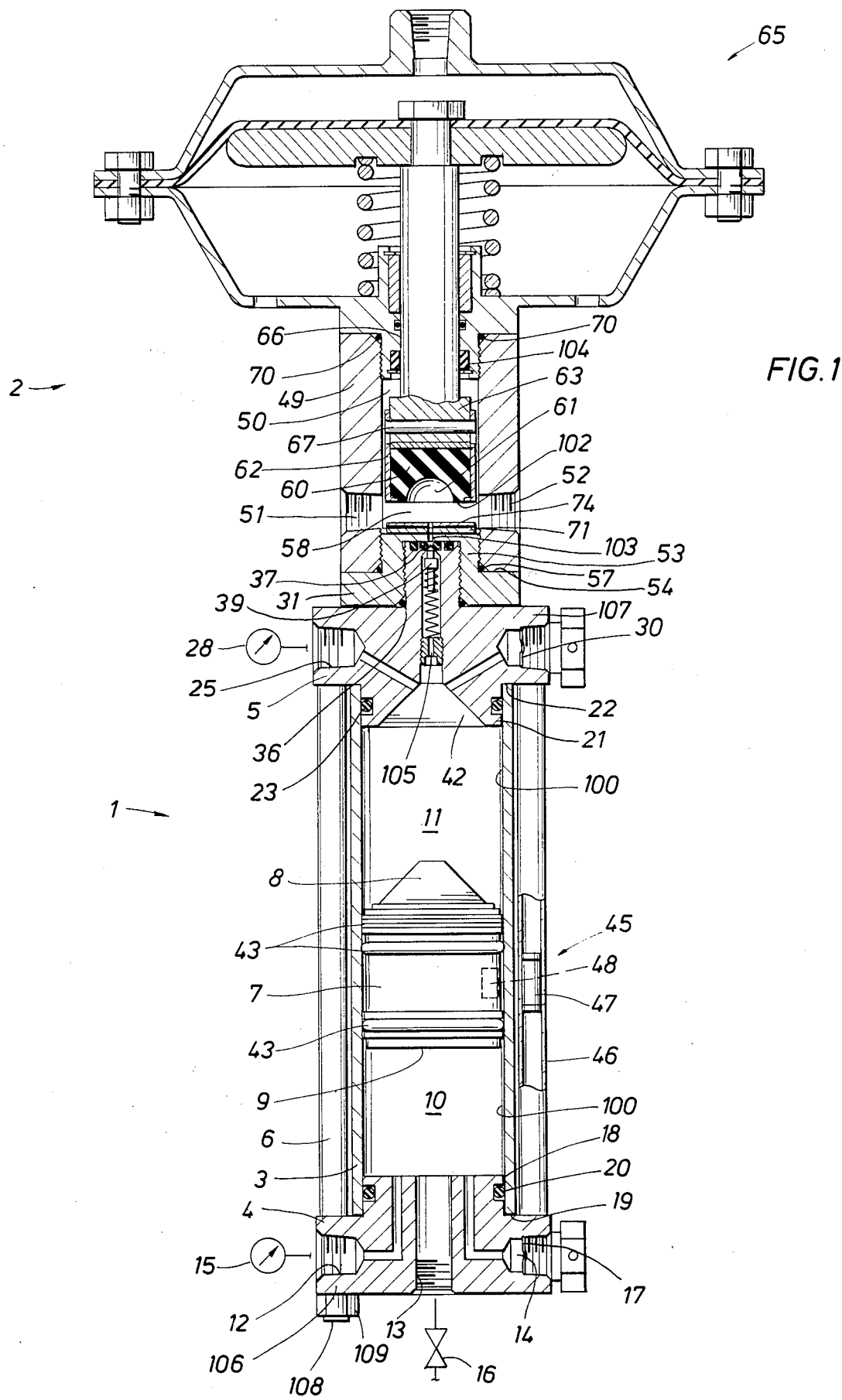
FIG. 1 is a section view of the integrated pump and sample vessel.

Referring to FIG. 1, and FIG. 2 the sample vessel is generally referred to with the numeral 1 and the pump is generally referred to with the numeral 2. The sample vessel is used to store aliquot samples of a fluid which have been transferred to the sample vessel by the pump 2. The sample vessel 1 includes a cylinder 3 which is captured between a precharge end cap 4 and a product end cap 5. The end caps 4 and 5 are secured to one another by a plurality of tie rods 6. Precharge end cap 4 has a circular flange 106 which is perforated by a plurality of holes (not shown in the drawing) through which tie rods 6 pass. Product end cap 5 has a circular flange 107 which is drilled and tapped with a plurality of holes (not shown in the drawing) to receive the threaded end portion (not shown in the drawing) of tie rods 6. The opposite end portion 108 of tie rods 6 is threaded to receive nut 109. When assembled, the nut 109 exerts force on flange 106 and flange 107 through tie rod 6 thus capturing the cylinder 3 between precharge end cap 4 and product end cap 5. A piston 7 is located within the cylinder 3. A conical protrusion 8 extends from one end of the piston 7; the other end of the piston is a flat surface 9. A precharge chamber 10 is defined by the flat side of the piston 9 the inside wall 100 of cylinder 3 and the precharge end cap 4. A product chamber 11 is defined by the conical protrusion 8 from the piston 7, the inside wall 100 of cylinder 3, and the product end cap 5.

The precharge end cap 4 has three ports therein, 12, 13, and 14 which communicate with the precharge chamber 10. Port 12 has a pressure gauge 15 attached thereto which measures and displays the pressure in the precharged chamber 10. Port 13 has a valve 16 attached thereto which isolates the precharge chamber 10 from the atmosphere. Port 14 has a sacrificial bursting relief member 17 attached thereto which will controllably rupture if the pressure in the precharge chamber 10 exceeds a predetermined limit. A cylindrical protrusion 18 extends from and is a part of the precharge end cap 4. The cylinder 3 slips over the cylindrical protrusion 18 and abuts the precharge end cap 4 at shoulder 19. A seal means 20 is located between the cylinder 3 and the cylindrical protrusion 18 to prevent entry or exit of fluid from the precharge chamber 10 at the shoulder 19.

Figure 6:
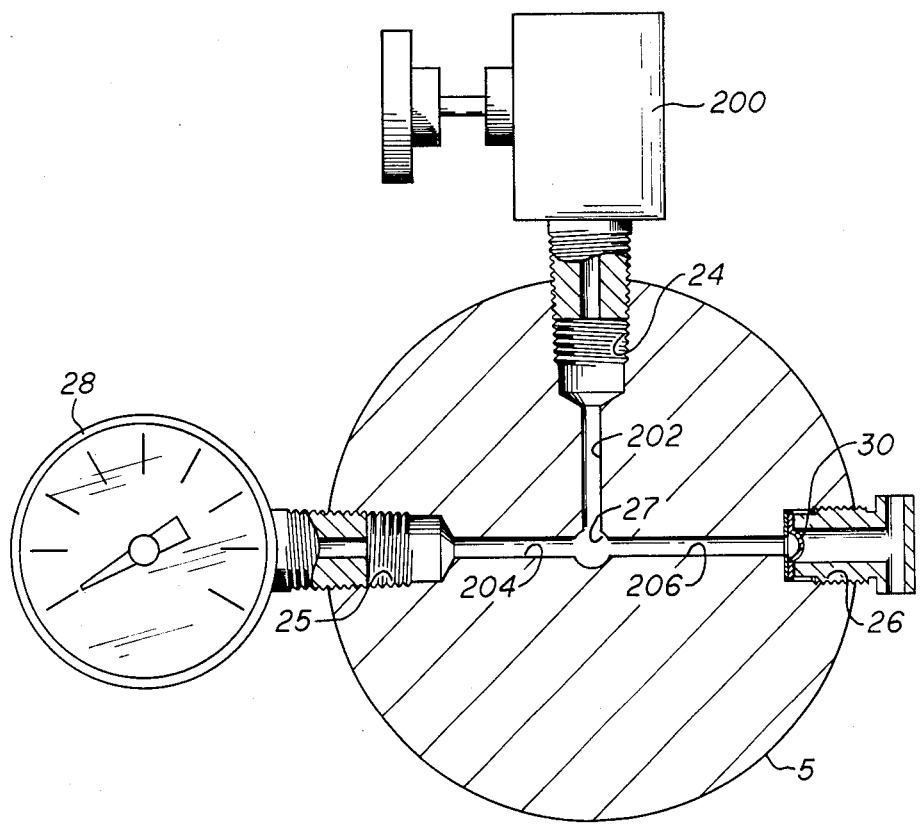
FIG. 6 is a diagrammatic view of the product end cap showing the ports therein and the connecting passageways which allow communication with the product chamber.

A second cylindrical protrusion 21 extends from and is a part of product end cap 5. The cylinder 3 slips over the cylindrical protrusion 21 and abuts the product end cap 5 at shoulder 22. A seal means 23 is located between the cylinder 3 and the second cylindrical protrusion 21 to prevent entry or exit of fluid from the product chamber 11 at shoulder 22. The product end cap 5 has four ports 24, 25, 26 and 27 located therein which communicate with the product chamber 11. Port 24, as best shown in FIG. 6, connects to a valve 200 which serves as an outlet for fluids contained within product chamber 11. Port 25 connects to a pressure gauge 28 which measures and displays the fluid pressure in product chamber 11. Port 26 connects to a bursting relief member 30 which will rupture if the fluid pressure in product chamber 11 exceeds a predetermined limit. Port 27 is the inlet to the product cavity 11 which receives fluid from the pump 2. An adapter 31 threadably engages the neck 32 which extends from and is a part of the product end cap 5. The adapter 31 abuts product end cap 5 at the shoulder 33 and end surface 101. The adapter 31 has a bevel 34 which forms a cavity 35 at the junction of the shoulder 33 and neck 32. A seal means 36 is located in cavity 35. A plurality of seal means 37 are located between the end surface 101 of neck 32 and the adapter 31.

The inlet port 27 is bored through the product end cap 5, the neck 32 and the end surface 101. A check valve means generally identified by the numeral 38 is located inside the inlet port 27. The check valve means 38 consists of the seal means 37 captured between the adapter 31 and the end surface 101 of neck 32, a poppet 39, a spring 40 and a spring retainer 41 which has a hole 105 bored through the center thereof. The spring urges the poppet 39 into sealing engagement with the seal means 37 which prevents the flow of fluid out of product chamber 11. When the pressure exerted by the pump 2 overcomes the force of spring 40, the poppet 39 moves away from seal means 37 and allows fluid to pass into product chamber 11. The product end cap 5 has a conical depression 42 made to receive the conical protrusion 8 on piston 7. The piston 7 has a plurality of seal means 43 located along its circumference which seal and isolate any fluids contained within the product chamber 11 from any fluids contained within the precharge chamber 10.

During the sampling process, it is desirable that certain hydrocarbon samples be kept under pressure in order that the laboratory to be able to effectively evaluate the nature of the sample. The following mode of operation is, therefore, recommended under certain circumstances. The product chamber 11 is vented to atmosphere and the precharged chamber 10 is pressurized. The forces acting on the piston 7 force it to move longitudinally in the cylinder such that the conical protrusion 8 is in direct contact with the conical depression 42 located in the product end cap 5. The effective area of product chamber 11 is then eliminated. The sample vessel 1 is then taken to the field and connected to the pump 2. The pump 2 then transfers fluid under pressure past the check valve means 38 into the product chamber 11. The pressure exerted by the pump is greater than the pressure in the precharged chamber 10. The forces acting on the piston 7 therefore cause it to move longitudinally in the cylinder away from product end cap 5 allowing sufficient space for the sample in product chamber 11. The sample is stored in product chamber 11 under pressure exerted by piston 7.

Because of the pressures involved, the cylinder 3 is typically made of metal or other non-transparent material. It is therefore desirable to have a tracker system generally designated by the numeral 45 which discloses the location of the piston 7 inside of cylinder 3. A tracker tube 46 is captured between the shoulder 19 on the precharge end cap 4 and the shoulder 22 on the product end cap 5. The tracker tube is made out of transparent material so that the tracker magnet 47 which travels longitudinally inside the tube can be readily observed. A second magnet 48 is located inside of the piston 7. The tracker magnet 47 is attracted to the piston magnet 48 which causes the tracker magnet 47 to move inside the tracker tube 46 as the piston moves inside of the cylinder 3. An observer can therefore determine where the piston 7 is located inside the cylinder 3 by the location of the tracker magnet 47 inside of the tracker tube 46.

The pump generally referred to by the numeral 2 includes of a body 49 with a longitudinal bore 50 therethrough. The inlet port 51 to the pump is located in the body 49 and communicates with the longitudinal bore 50. The outlet port 52 is likewise located in the body 49 and communicates with longitudinal bore 50. The adapter neck 53 threadably engages the longitudinal bore 50 and abuts the body 49 at shoulder 54. The corner 55 of the body 49 contains a slight bevel which creates a cavity 56 between the body and the shoulder 54. A seal means 57 is located in cavity 56 to prevent the escape of fluid from the longitudinal bore 50 in the body 49 of the pump 2. A passage 58 exists in the body 49 of the pump 2 which allows fluid to flow through the inlet port 51, through passage 58 and out through the outlet port 52.

A resilient member 60 is located in the longitudinal bore 50 opposite the face 59 of the adapter 31. The face 102 of the resilient member has a cavity 61 therein which is exposed to the passage 58 in the pump body 49. A hollow sleeve 62 confines the resilient member 60 and prevents extrusion when pressure is applied to the resilient member 60. A shaft 63 is located in the longitudinal bore 50 of the body and can be actuated by various conventional moving means, i.e., solenoids, diaphragm motors, or electric motors. In FIG. 1, a diaphragm motor generally referred to by the numeral 65 is shown connected to the shaft 63. The shaft 63 is aligned in the bore 50 by bearing surface 66. A holding pin 67 extends through a slot 69 in hollow sleeve 62 and attaches the sleeve to the shaft 63. The hollow sleeve 62 contains a shoulder 68 which partially covers the face 102 of the resilient member 60. The cavity 61 is not covered by the shoulder 68. A seal means 70 is located between the body 49 and the diaphragm motor 65 to prevent escape of fluid from the longitudinal bore 50 of the pump 2. A seal means 104 is located between the bearing surface 66 and the shaft 63 to prevent the escape of fluid from the longitudinal bore 50 of the pump 2.

In FIG. 3, a thin circular vacuum breaker plate 71 is shown with radial slots 72 which extend therethrough. The plate 71 has a hole 73 extending through the center thereof. The plate 71 is preferably made out of Kel-F or other resilient material.

In FIG. 4 a second thin circular plate 74 is shown with a hole 75 extending through the center thereof. The second plate 74 can be made of metal or a resilient material such as Kel-F. Circular plate 71 lays on the face 59 of the adapter 31. Plate 74 lays on top of plate 71 like a stack of pancakes. The pump 1 will function without either of the vacuum breaker plates 71 and 74; however, if vacuum breaker plates are not employed the life of the resilient member 60 will be substantially reduced due to increased internal stresses.

Figure 5:
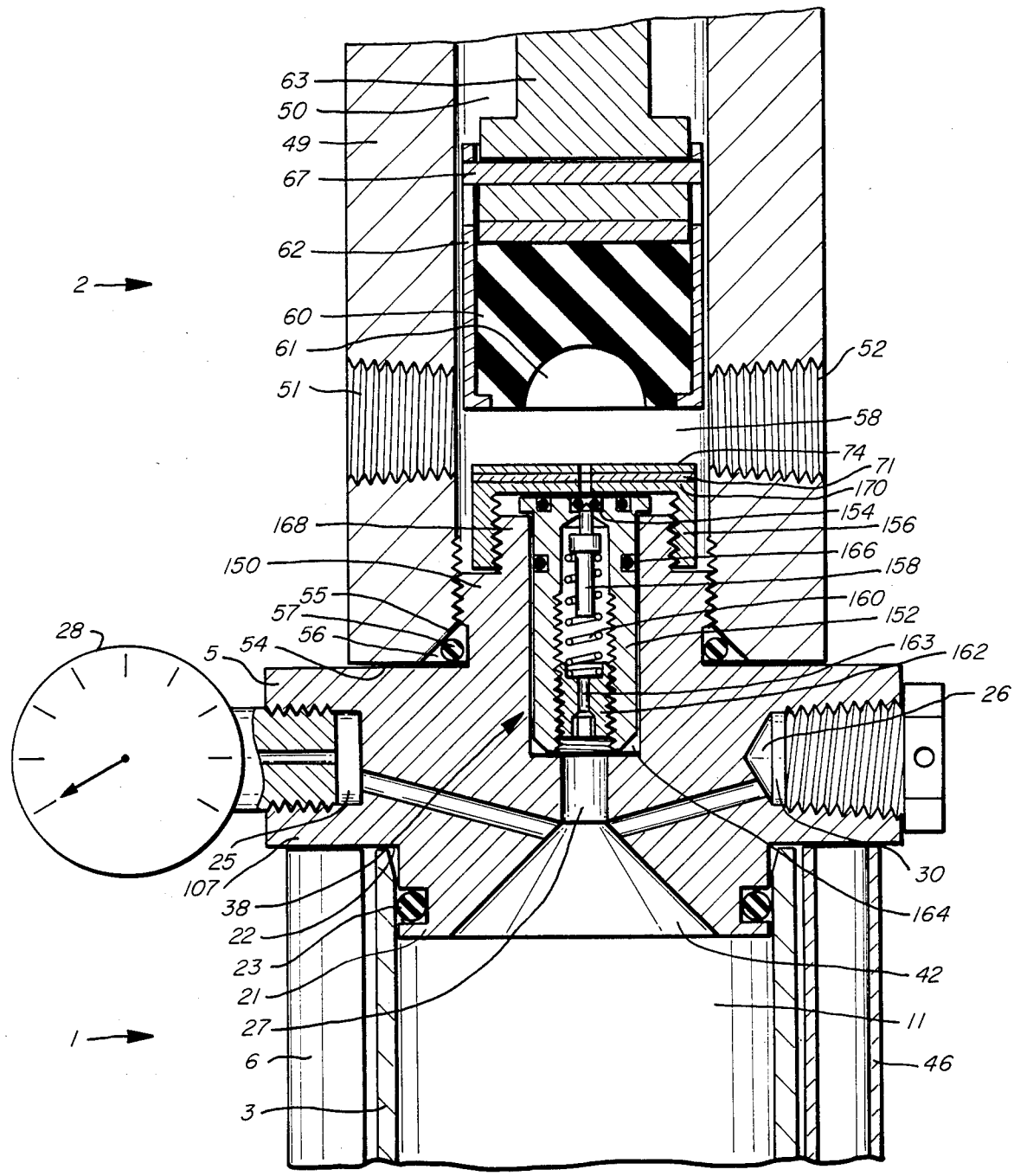
FIG. 5 is a section view of an alternative embodiment of the integrated pump and sample vessel.

In FIG. 5, a section view of an alternative embodiment of the integrated pump and sample vessel is shown. In this alternative embodiment, the adapter 31 is deleted. Instead, a neck 150 which extends from and is a part of the product end cap 5, threadably engages the body 49 of the sampler and abuts same at shoulder 54. The check valve means 38 is contained within a removable pod 152. The pod 152 fits inside of a bore 164 which extends through the neck 150 and the product end cap 5 and connects with the inlet port 27. The removable pod 152 is held in place by a seal retainer 156 which threadably engages a cylindrical extension 168 from neck 150. Plates 74 and 71 lay respectively like pancakes on the exposed surface 170 of the seal retainer 156. The check valve means 38 consists of a seal means 154 captured between the seal retainer 156 and the removable pod 152, a poppet 158, a spring 160, and a spring retainer 162 which has a hole 163 bored through the center thereof. When the seal retainer 156 has been removed from the cylindrical extension 168, the entire pod 152 and check valve means 38 can be removed from the product end cap 5 for service or adjustment. This easy access facilitates maintenance and service. In the embodiment shown in FIGS. 1 and 2, the entire sample vessel 1 must be disassembled in order to service or adjust the check valve means 38. For these reasons, the embodiment shown in FIG. 5 is preferred.

FIG. 6 is a diagrammatic view of the product end cap 5. Port 27 is the inlet to the product cavity 11, better shown in FIG. 1. The product cavity 11 receives fluid from the pump 2. In FIG. 6, valve 200 threadably engages port 24. A passageway 202 connects the port 24 with the inlet port 27, thereby allowing fluid to pass from the product cavity 11, through the inlet port 27, the passageway 202, and the valve 200. A pressure gauge 28 threadably engages port 25. A passageway 204 connects the port 25 with the inlet port 27, thereby allowing the pressure gauge 28 to sense and measure the fluid pressure, if any, within product cavity 11. A bursting relief member 30 is mounted in port 26. A passageway 206 connects the port 26 with the inlet port 27 thereby allowing the pressurized fluid, if any, in the product cavity 11 to act upon the bursting relief member.

OPERATION

The following discussion will explain one operational stroke of the pump 2 placing an aliquot of sample fluid into the sample vessel 1. As shown in FIG. 1, the pump is in a relaxed state. The diaphragm motor 65 is actuated causing the shaft 63 to move the resilient member 60 and the hollow sleeve 62 into direct contact with plate 74 which lays on the top of plate 71, which lays on the face 59 of the adapter 31. The initial pressure applied by the shaft 63 causes a seal to be formed between the resilient member 60, plates 71 and 74, and the face 59 of adapter 31 which traps an aliquot of sample in the cavity 61 of resilient member 60. As the diaphragm motor 65 continues to drive the shaft 63, greater pressure is exerted upon the resilient member 60 which causes the cavity 61 to collapse, forcing the aliquot sample through the holes 75 and 73 in the plates 74 and 71 respectively, through the hole 103 in the face of adapter 31, and past the check valve means 38 into the product chamber 11. Because the pressure exerted by the diaphragm motor 65 exceeds the pressures in the precharge chamber 10, the piston 7 will move longitudinally in the cylinder 3 as the aliquot samples are collected. The slot 69 located in the hollow sleeve 62 allows the holding pin 67 a degree of freedom so that the shaft 63 can advance to collapse the cavity 61 in the resilient member 60 without collapsing the hollow sleeve 62. After the aliquot sample has been pumped into the sample vessel 1, the diaphragm motor 65 relaxes and begins to retract the shaft 63 and attached hollow sleeve 62 and resilient member 60 away from plates 74, 71, and the face 59 of the adapter. The vacuum breaker plate 74 and plate 71 will rise slightly in the passage 58 as the shaft 63 raises the resilient member 60. A temporary vacuum created in the cavity 61 will immediately be broken as fluid passes into slots 72 and through the holes 73 and 75 in plates 71 and 74 into the cavity 61, causing the plates 71 and 74 to separate from the resilient member 60. The vacuum breaker plate 71 and plate 74 will remain in their resting place on the face 59 of the adapter 31 as a result of the pull of gravity or a friction fit in the bore. The diaphragm motor 65 continues to retract the shaft 63 to its relaxed position such that the passage 58 is again open to allow the flow of fluid from the inlet port 51 to the outlet port 52 through the bore 50 in body 49 of the pump 2.

In FIG. 5, an alternative embodiment of the integrated pump 2 and sample vessel 1 is shown. The same diaphragm motor 65 shown in FIG. 1 is present in the alternative embodiment and for the sake of brevity has been omitted from FIG. 5. Likewise, the lower portion of the sample vessel 1 shown in FIG. 1 is omitted from FIG. 5.

The product end cap 5 has a neck 150 which threadably engages the longitudinal bore 50 and abuts the body 49 at shoulder 54. The corner 55 of the body 49 contains a slight bevel which creates a cavity 56 between the body 49 and the shoulder 54. A seal means 57 is located in cavity 56 to prevent the escape of fluid from the longitudinal bore 50 in the body 49 of the pump 2.

The check valve means generally identified by the numeral 38 is located in removable pod 152. The check valve means 38 consists of the seal means 154 captured between the seal retainer 156 and the pod 152, a poppet 158, a spring 160 and a spring retainer 162. A hole 163 extends through the longitudinal center of spring retainer 162. The spring 160 urges the poppet 158 into sealing engagement with the seal means 154 which prevents the flow of fluid out of product chamber 11. When the pressure exerted by the pump 2 overcomes the force of spring 160, the poppet 158 moves away from seal means 154 and allows fluid to pass into product chamber 11. The removable pod 152 slips into a bore 164 which runs through neck 150 and connects with the inlet port 27 and the product chamber 11. A seal means 166 is located between the pod 152 and the bore 164 to prevent the escape of fluids from product chamber 11.

The seal retainer 156 threadably engages a cylindrical extension 168 which extends from and is part of neck 150 which extends from and is part of product end cap 5. The vacuum breaker plate 71 lays on the face 170 of seal retainer 165. The vacuum breaker plate 74 lays on vacuum breaker plate 71 in pancake fashion. The alternative embodiment shown in FIG. 5 operates in a similar fashion to the embodiment described in FIG. 1.

There are two primary differences between the two embodiments. In the alternative embodiment shown in FIG. 5, the check valve means 38 can be conveniently accessed by unscrewing the seal retainer 156 and removal of the pod 152 for maintenance or adjustment. In the embodiment shown in FIG. 1, the entire sample vessel 1 must be disassembled for service or adjustment of the check valve means 38.

The second difference between these embodiments relates to the manner of attachment of the sample vessel 1 to the pump 2. In the alternative embodiment shown in FIG. 5, an enlarged neck 150 directly engages the bore 50 of pump 2. In the other embodiment, a smaller neck 32 engages an adapter 31 which directly engages the bore 50 of pump 2.

While the foregoing is directed to the preferred embodiment of the present invention, other and further embodiments of the invention may be devised without departing from the basic scope thereof, and the scope thereof is determined by the claims which follow.

What is claimed is:

1. An integrated pump and sample vessel comprising:
   a body with a longitudinal bore therethrough;
   a passage in said body allowing fluid to enter and exit said body;
   a vessel for the storage of samples taken from said fluid;
   check valve means located in said vessel to selectively enable the entry of fluid from said passage into said vessel;
   an adapter for detachably mounting said vessel on said body, said adapter having a face exposed to said passage;
   a resilient member located in said bore having a face with a cavity therein exposed to said passage;
   a hollow sleeve confining said resilient member; and
   means for relatively moving said face of said resilient member in said passage into contact with said face of said adapter for trapping a sample of fluid in said cavity, said moving means resiliently collapsing said cavity which pumps sample past said check valve means and into said vessel.

2. The apparatus of claim 1 including a means to relieve over pressures in said vessel.

3. The apparatus of claim 2 including a means to measure pressure in said vessel.

4. The apparatus of claim 1 including a piston located in said vessel which divides said vessel into two separate chambers.

5. The apparatus of claim 4 wherein,
   said piston has a conical protrusion therefrom which fits into a conical depression in said vessel.

6. The apparatus of claim 4 including:
   means to track said piston moving in said vessel; and
   means to display on the exterior of said vessel the moving location of said piston.

7. An integrated pump and sample vessel comprising:
   a body with a longitudinal bore therethrough;
   a passage in said body allowing fluid to enter and exit said body;
   a vessel for the storage of samples taken from said fluid;
   check valve means located in said vessel to selectively enable the entry of fluid from said passage into said vessel;
   an adapter for detachably mounting said vessel on said body, said adapter having a face exposed to said passage;
   a resilient member located in said bore having a face with a cavity therein exposed to said passage;
   a hollow sleeve confining said resilient member;
   means to break a vacuum between said face of said adapter and said face of said resilient member; and
   means for relatively moving said face of said resilient member in said passage toward said face of said adapter and into contact with the vacuum breaking means for trapping a sample of fluid in said cavity, said moving means resiliently collapsing said cavity which pumps sample past said check valve means and into said vessel.

8. The apparatus of claim 7 including means to relieve over pressures in said vessel.

9. The apparatus of claim 8 including means to measure pressure in said vessel.

10. The apparatus of claim 7 including a piston located in said vessel which divides said vessel into two separate chambers.

11. The apparatus of claim 10 wherein,
said piston has a conical protrusion therefrom which fits into a conical depression in said vessel.

12. The apparatus of claim 11 including:
means to track said piston moving in said vessel; and
means to display on the exterior of said vessel the moving location of said piston.

13. A sampling system comprising:
a. a detachable sample vessel including;
  (i) an elongate tube having a first end cap and a second end cap defining a sample storage chamber;
  (ii) said first end cap of said tube having a cylindrical neck extending therefrom, said neck having a smaller diameter than said tube and said neck having a pocket formed therein;
  (iii) check valve means contained in a removable pod, said pod contoured to fit into said pocket of said first end cap, to selectively enable the entry of a fluid into said sample storage chamber;
  (iv) restraining means detachably mounting on said neck of said first end cap of said tube to restrain said pod in said pocket, said restraining means having a face thereon;
b. a pump including;
  (i) a body with a longitudinal bore therethrough;
  (ii) a passage in said body allowing said fluid to enter and exit said body;
  (iii) a resilient member located in said bore having a face with a cavity therein exposed to said passage;
  (iv) a hollow sleeve to confine said resilient member; and
  (v) means for relatively moving said face of said resilient member towards said face of said restraining means for trappaing a sample of fluid in said cavity, said moving means resiliently collapsing said cavity which pumps said sample past said check valve means and into said sample storage chamber; and
c. means for detachably mounting said sample vessel on said pump to expose said face of said restraining means to said passage.

14. The apparatus of claim 13 including a plurality of vacuum breaker plates having holes therein positioned between the face of said resilient member and the face of said vessel.

15. The apparatus of claim 13 including:
means to relieve over pressures in said vessel.

16. The apparatus of claim 13 including:
means to measure pressure in said vessel.

17. The apparatus of claim 13 including a piston located in said vessel which divides said sample storage chamber into a first compartment and a second compartment.

18. The apparatus of claim 17 wherein,
said piston has a conical protrusion therefrom which fits into a conical depression in said first end cap of said tube.

19. The apparatus of claim 18 including,
means to track said piston moving in said sample storage chamber; and
a means to display on the exterior of said vessel the moving location of said piston.

* * * * *